United States Patent [19]

Murakami et al.

[11] Patent Number: 5,254,470

[45] Date of Patent: Oct. 19, 1993

[54] ALKALINE PROTEASE, ALKALINE PROTEASE GENE, RECOMBINANT DNA, DNA FRAGMENT FOR THE EXPRESSION OF GENE, AND PROCESS FOR THE PRODUCTION OF ALKALINE PROTEASE

[75] Inventors: Seiji Murakami; Hiroki Tatsumi; Yoshihiro Ogawa; Eiichi Nakano; Hiroshi Motai, all of Noda; Shigetoshi Sugio, Hirakata; Atsushi Masaki, Hirakata; Yutaka Ishida, Hirakata; Kohji Murakami, Hirakata; Haruhide Kawabe, Hirakata; Hirofumi Arimura, Hirakata, all of Japan

[73] Assignee: Japanese Research and Development Association for Improvement of Enzyme Function in Food Industry, Japan

[21] Appl. No.: 672,304

[22] Filed: Mar. 20, 1991

[30] Foreign Application Priority Data

Mar. 23, 1990 [JP] Japan .................................. 2-71810

[51] Int. Cl.⁵ .................... C12N 9/62; C12N 15/51
[52] U.S. Cl. .................................. 435/225; 435/224; 435/221; 435/222; 536/23.2
[58] Field of Search .............. 435/224, 225, 226, 222; 536/29, 23.2

[56] References Cited

U.S. PATENT DOCUMENTS 4,760,025  7/1985  Estely et al. .................... 435/222

FOREIGN PATENT DOCUMENTS 73038873  9/1970  Japan .
2002374   7/1988  Japan .
2002375   7/1988  Japan .

OTHER PUBLICATIONS

Tatsumi, H., et al, (1989) Mol. Gen. Genet, 219, 33–38.
Fukushima, et al., Agric. Biol. Chem., vol. 49, No. 6, 1985, Abstract only.
Murakami, et al., Nippon Nogei Kagaku Kaisha, vol. 64, 1990, p. 267, Abstract No. 3Ba10.

Primary Examiner—Charles L. Patterson, Jr.
Attorney, Agent, or Firm—Banner, Birch, McKie & Beckett

[57] ABSTRACT

Alkaline protease which has leucine or isoleucine in the place of valine at the amino acid number 40 of wild type alkaline protease, a gene encoding the amino acid sequence of alkaline protease which has the substitution as described above, a recombinant DNA comprising said gene, a method of producing the above described alkaline protease, and a DNA fragment used for the expression of a gene.

4 Claims, 4 Drawing Sheets

ALKALINE PROTEASE, ALKALINE PROTEASE GENE, RECOMBINANT DNA, DNA FRAGMENT FOR THE EXPRESSION OF GENE, AND PROCESS FOR THE PRODUCTION OF ALKALINE PROTEASE

FIELD OF THE INVENTION

This invention relates to alkaline protease, alkaline protease gene, novel recombinant DNA, a prepro region for the expression of the alkaline protease gene and a method for the production of alkaline protease.

PRIOR ART

There has been no report on the structure of an alkaline protease gene derived from *Aspergillus oryzae* which is a member of yellow koji mold. Even the isolation of this gene remained to be accomplished before the present invention.

The alkaline protease is a hydrolase capable of hydrolyzing a protein or a partial hydrolyzate thereof to cleave the peptide bond thereof. It can be used extensively in pharmaceuticals, foods, beverages, detergents, etc.

SUMMARY OF THE INVENTION

The object of the present invention is to provide alkaline protease in which valine at the amino acid number 40 of the wild type alkaline protease is replaced by leucine or isoleucine, alkaline protease gene encoding the above described amino acid sequence having amino acid substitution, recombinant DNA containing said gene, a DNA fragment used for the expression of a gene and a method of producing said alkaline protease having the above described amino acid substitution.

The inventors have investigated the alkaline protease gene derived from *Aspergillus oryzae* and have succeeded for the first time in isolating the alkaline protease gene and a prepro type alkaline protease gene, and determined the structures thereof (Japanese Patent Appln. Laid-Open-to-Public Publication Nos. 2374/1990 and 2375/1990, and Japanese Patent Appln. Nos. 280370/1989 and 280371/1989).

More recently, the inventors have tried to find an efficient method of producing alkaline protease using the prepro type alkaline protease gene and surprisingly found that by culturing *Saccharomyces cerevisiae* harboring a recombinant plasmid containing the prepro type alkaline protease gene derived from *Aspergillus oryzae*, alkaline protease could be produced by the microorganism and secreted from the host into a culture medium (Japanese Patent Appln. Nos. 280372/1989 and 280373/1989).

We have further tried to find a method of producing alkaline protease of increased activity and successfully found that introduction of mutation into the alkaline protease gene results in a great increase in the activity of the alkaline protease produced. We have prepared a gene encoding alkaline protease having leucine or isoleucine in the place of valine at amino acid number 40 of wild type alkaline protease and inserted the gene into a suitable expression vector. The resultant construct is used to transform a microorganism belonging to the genus Saccharomyces and the transformants formed are cultured. Alkaline protease recovered from the culture has about 1.6-1.7-fold elevated activity. In addition, a construct containing the prepro sequence for an alkaline protease gene also expresses the gene encoding said protease having the amino acid substitution as mentioned above.

The amino acid sequence of wild-type alkaline protease is described in Japanese Patent Appln. LOP Publn. No. 2374/1990.

The present invention is directed to alkaline protease in which valine at the amino acid number 40 of wild type alkaline protease is replaced by leucine or isoleucine, to an alkaline protease gene encoding said amino acid sequence having amino acid substitution, to a novel recombinant DNA containing said gene, a transformant of Saccharomyces containing the recombinant DNA, and a method of producing alkaline protease by culturing the transformant and recovering alkaline protease from the culture. The present invention also provides a DNA fragment which contains a prepro sequence encoding the amino acid sequence as defined in the Sequence Listing by SEQ ID NO: 1, and which is used for the expression of a gene encoding a polypeptide such as alkaline protease.

The present invention will be described in detail hereinafter.

An alkaline protease gene used in the present invention is derived, for example, from *Aspergillus oryzae* (ATCC 20386).

*Aspergillus oryzae* is cultured according to the method as described in Japanese Patent Publication No. 38873/1973, and the cells are harvested from the culture using the methods known in the art, e.g., filtration, centrifugation, etc.

Cells are ruptured using glass beads and extracted with phenol. mRNA is then prepared according to the known methods (for example, Maniatis, T., 1982, Molecular Cloning, A Laboratory Manual, Cold Spring Harbor Laboratory, Cold Spring Harbor, N.Y.; Koseki, H. and Shimura, S., 1983 Experimental Procedure for Molecular Genetics p66-67). mRNA of alkaline protease is screened from the resultant mRNA according to a known method such as described in Biomedical Research, 1982, 3: 534-540, using anti-alkaline protease serum prepared according to the method described by Yamamura, Y., 1973, Immunochemistry, p43-50.

Alkaline protease mRNA is used to prepare cDNA according to the methods (Mol. Cell. Biol., 1982, 2: 161; Gene, 1983, 25: 263). cDNA thus obtained is inserted into a vector DNA such as pUC 119 (Takara Shuzo Co. LTD) to prepare a recombinant plasmid which is then used to transform various microorganisms such as *E. coli* DH1 (ATCC 33849), *E. coli* HB101 (ATCC 33694), and the like according to the method as described by Hanahan, 1985, DNA Cloning, 1: 109-135.

A recombinant plasmid containing alkaline protease cDNA is selected from transformants according to the hybridization-selection method (Maniatis, T., 1982, Molecular Cloning, A Laboratory Manual, Cold Spring Harbor Laboratory, Cold Spring Harbor, N.Y.): cDNA containing a partial alkaline protease sequence is labelled with $^{32}P$ according to the nick translation method (Maniatis, T., 1982, Molecular Cloning, A Laboratory Manual, Cold Spring Harbor Laboratory, Cold Spring Harbor, N.Y.); (J. Mol. Biol., 1977, 113: 237-251). The labelled cDNA is used as a probe to screen the cDNA library according to the colony hybridization method (Protein, Nucleic Acid, Enzyme, 1981, 26: 575-579), and a recombinant plasmid containing a 1.5 kb cDNA fragment encoding alkaline protease is obtained.

A fragment containing a prepro sequence and an alkaline protease cDNA (prepro-type alkaline protease DNA) is obtained as follows: Plasmid containing the 1.5 kb cDNA fragment is digested with a restriction enzyme such as EcoRI at 30°–40° C. preferably at 37° C. for 1–24 hours preferably for 2 hours. The restriction fragments are electrophoresed on an agarose gel according to the method described by Maniatis, T., 1982, Molecular Cloning, A Laboratory Manual, Cold Spring Harbor Laboratory, Cold Spring Harbor, N.Y., p. 150. A DNA fragment containing the prepro-type alkaline protease DNA derived from *Aspergillus oryzae* is obtained.

The DNA recovered is sequenced according to the method described in Example (11) and shown in SEQ ID NO: 5, and the amino acid sequence is deduced from the nucleotide sequence (FIG. 6) as shown in SEQ ID NO: 6.

Vector DNA is digested with an enzyme such as EcoRI (Takara Shuzo Co. LTD) at 30°–40° C. preferably at 37° C. for 1–16 hours preferably for 2 hours. The digest is ligated to the prepro-type alkaline protease DNA using a DNA ligase such as T4 DNA ligase (Takara Shuzo Co. LTD) according to the method known in the art.

Any vector may be used (e.g., MA56 available from Washington Research Foundation). The construct thus produced is used to transform microorganisms belonging to the genus Saccharomyces (e.g., *Saccharomyces cerevisiae* SHY1 (ATCC 44769)) according to the method described by Beggs (Nature 275: 104–109 (1978)). A transformant capable of secreting alkaline protease is obtained. Recombinant DNA is prepared from the transformant according to the method (Proc. Natl. Acad. Sci. 1969, 62: 1159–1166).

In the recombinant DNA, the codon GTG (nucleotide numbers 118–120) corresponding to valine at the amino acid number 40 of wild type alkaline protease can be replaced by ATT or CTG corresponding to leucine or isoleucine, respectively, by site directed mutation using for example oligonucleotide-directed in vitro mutagenesis system version 2 (Amersham).

DNAs of the desired mutants are digested with restriction enzymes such as BglII and AflII according to the method known in the art to prepare alkaline protease DNAs having the desired mutation.

The promoter and terminator (generous gift from Prof. Toe of Hiroshima University) of glyceraldehyde-3-phosphate dehydrogenase (GAPDH) derived from *Zygosaccharomyces rouxii*, the prepro-type alkaline protease cDNA and a vector DNA are ligated using, for example T4 DNA ligase (Takara Shuzo Co. LTD).

Any vector may be used for the above ligation such as pOAP106B as described in Example hereinafter. The vector is digested with, for example, BglII and AflII, and ligated to the fragment containing the mutation using a DNA ligase such as T4 DNA ligase (Takara Shuzo Co. LTD). The resultant construct is used to transform *Saccharomyces cerevisiae* strain such as *S. cerevisiae* NA87-11A (generous gift from Prof. Oshima of Osaka University) as described by Beggs (Nature 275: 104–109 (1978)).

The transformant thus obtained has ability to produce alkaline protease. The recombinant DNA having the desired mutation is prepared from the transformant according to the method (Proc. Natl. Acad. Sci., 1969, 62: 1159–1166).

The transformant can then be cultured in a medium and alkaline protease can be recovered from the culture. Any culture medium conventionally used for the microorganisms belonging to the genus Saccharomyces may be utilized for example YPD medium (glucose, polypeptone, yeast extract).

A culture temperature is 25°–35° C., preferably 30° C. The incubation period is 6–120 hours, preferably 48 hours.

The culture is then centrifuged at 3,000 r.p.m. for about 2 minutes. The supernatant can be utilized as a crude enzyme solution. The cells may be disrupted by mixing in vortex mixer together with glass beads for about 3 minutes to yield crude enzyme solution.

Crude enzyme solution thus obtained can be used without further purification, or can be purified through the methods such as ammonium sulfate fractionation, ion exchange chromatography (e.g., DEAE-BioGel A), gel filtration (e.g., Ultro-Gel AcA34), etc., to prepare pure alkaline protease.

Alkaline protease with the substitution of leucine or isoleucine for valine at the amino acid number 40 has a 1.6–1.7 fold increase in its enzyme activity compared with wild type alkaline protease. The other physical and chemical properties of the mutant alkaline protease are the same as those described in Agr. Biol. Chem., 1973, 37: 2685–2694.

The nucleotide sequence encoding a prepro region (shown in the Sequence Listing by SEQ ID NO: 1) allows the expression of the alkaline protease gene with leucine or isoleucine substitution for valine, suggesting that the prepro sequence may be extremely useful for the expression of a gene.

Figure 1:
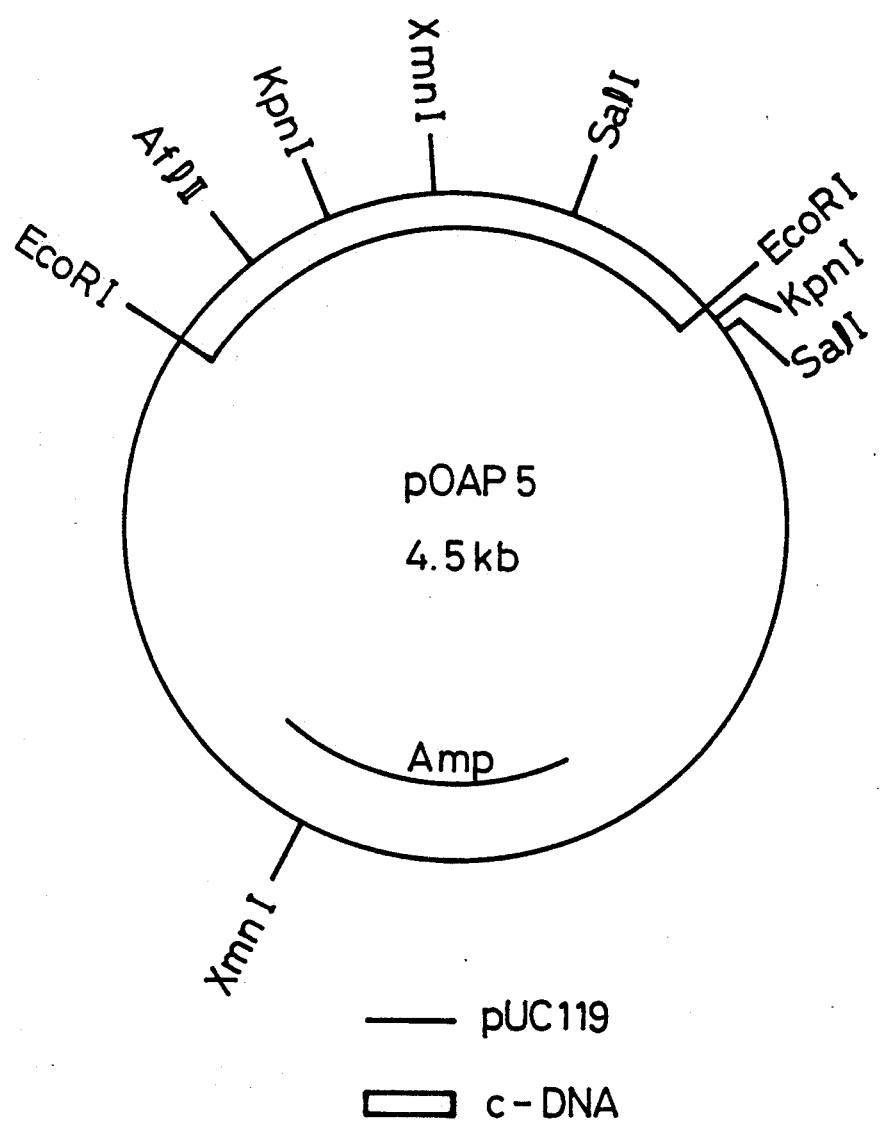
FIG. 1 shows the restriction map of a recombinant plasmid pOAP5.

As mentioned above, the present invention provides an industrially useful alkaline protease, and a method of efficiently producing the same by culturing a transformant of the genus Saccharomyces which carries a recombinant DNA, and recovering alkaline protease with increased activity from the culture.

The following Example further illustrates the invention.

EXAMPLE

(1) Production of Cells

*Aspergillus oryzae* (ATCC 20386) ($1.2 \times 10^8$ spores) was added to 50 ml of a medium [3% (W/V) heated, press-expanded nonfat soybean, and 3% (W/V) $KH_2PO_4$]. The mixture was then incubated in a shaker (M-100°, Taiyo Kagaku Kogyo Co.) at 120 r.p.m. for 45 hours at 30° C. Then, the culture was filtered to give 10 g of the cells.

(2) Isolation of mRNA 10 g of the cells obtained in (1) above were added to 20 ml of a guanidine isothiocyanate solution [6M guanidine isothiocyanate, 37.5 mM sodium citrate pH 7.0, 0.75% (W/V) N-lauroylsarcosine sodium, 0.15M β- mercaptoethanol]. The mixture was placed in a blender cup (Nippon Seiki Seisakusho Co.), and 10 g of glass beads (0.5 mm in diameter) was added to the cup. The mixture was stirred at 10,000 r.p.m. for 5 minutes. 10 ml of phenol equilibrated with water was added to the mixture. The mixture was centrifuged at 10,000 r.p.m. for 10 minutes to disrupt the cells.

Then, the resultant mixture was centrifuged (18PR-52®, Hitachi Koki Co.) at 5,000 r.p.m. for 10 minutes to give 20 ml of a supernatant.

1.2 ml aliquots of 5.7M cesium chloride were dispensed to four ultracentrifuge tubes (Hitachi Koki Co.). The supernatant as obtained above was layered onto the individual cesium chloride solutions, and the tubes were centrifuged (SCP55H, Hitachi Koki Co.) at 30,000 r.p.m. for 16 hours at 15° C. to give a pellet.

The combined pellet was rinsed with ice cold 70% (V/V) ethanol, and then resuspended in 4 ml of 10 mM Tris buffer [10 mM Tris/HCl pH 7.4, 5 mM EDTA, 1% sodium dodecylsulfate]. The suspension was extracted with an equal volume of n-butanol/chloroform (4:1 V/V) mixture. The extract was centrifuged at 3,000 r.p.m. for 10 minutes to separate layers. The organic layer was extracted with 4 ml of the same 10 mM Tris buffer and the extraction procedure was repeated twice. To the aqueous layer combined, 1/10 volume of 3M sodium acetate (pH 5.2) and 2 volumes of ice cold ethanol were added and the mixture was left standing at −20° C. for 2 hours. Then, the mixture was centrifuged at 8,000 r.p.m. for 20 minutes to precipitate RNA as a pellet. The pellet was resuspended in 4 ml of water, and precipitated with ethanol as described above. The resulting RNA was resuspended in 1 ml of water. 12 mg of RNA was obtained.

12 mg of RNA thus obtained was loaded onto the top of the oligo (dT) cellulose column (New England Biolab Co.).

The oligo (dT) column was prepared by filling a 2.5 ml Terumo syringe column (Terumo Corp.) packed with 0.5 g of resin which has previously been swelled in an elution buffer [10 mM Tris-HCl (pH 7.6), 1 mM EDTA, 0.1% (W/V) sodium dodecylsulfate]. The column was then equilibrated with a binding buffer [10 mM Tris-HCl (pH 7.6), 1 mM EDTA, 0.4M NaCl, 0.1% sodium dodecylsulfate].

An equal volume of a buffer [10 mM Tris-HCl (pH 7.6), 1 mM EDTA, 0.8M NaCl, 0.1% sodium dodecylsulfate] was added to the RNA solution containing 12 mg of the RNA. The mixture was incubated at 65° C. for 10 minutes, and then rapidly cooled on ice. Then, the mixture was loaded onto the oligo (dT)-Cellulose column. The column was washed with the binding buffer to remove unbound rRNA and tRNA completely. Then, mRNA was eluted using the elution buffer to give 90 μg of mRNA.

(3) Isolation of Alkaline Protease mRNA mRNA was concentrated using a sucrose density gradient centrifugation. The sucrose gradient [10-25% (W/V)] was made as follows: 0.5 ml of 40% (W/V) sucrose [50 mM Tris-HCl pH 7.5, 20 mM NaCl, 1 mM EDTA, 40% (W/V) sucrose] was placed in a polyaroma tube for SW 41 Rotor (Beckman). Then, 2.4 ml of each of sucrose solution (25% (W/V), 20% (W/V), 15% (W/V), 10% (W/V)) was layered and left standing at 4° C. for 24 hours. 50 μg of mRNA was layered onto the sucrose gradient. The tube was ultracentrifuged at 30,000 r.p.m. at 18° C. for 18 hours using Beckman SW 41 Rotor. After centrifugation, a total volume was removed in 0.5 ml fractions. Ethanol was added to each fraction to precipitate mRNA. The precipitate was recovered and resuspended in 10 μl of water.

The fraction containing a high level of alkaline protease mRNA was selected as follows: 1 μl of the fraction, 9 μl of rabbit reticulocyte lysate (Amersham) and 1 μl of $^{35}$S-methionine (Amersham) were combined and incubated at 30° C. for 30 minutes. 150 μl of NET buffer [150 mM NaCl, 5 mM EDTA, 0.02% (W/V) NaN$_3$, 20 mM Tris-HCl/pH 7.4, 0.05% (W/V) Nonidet P-40 (Bethesda Research Laboratory) was added to the mixture. Then, 1 μl of anti-alkaline protease serum (prepared as described below) was added, and the mixture was incubated at 4° C. for 18 hours. Then, 10 mg of Protein A Sepharose (Pharmacia) was added followed by incubation at 20° C. for 30 minutes. After incubation, the mixture was centrifuged at 12,000 r.p.m. for 1 minute. The pellet was recovered and washed 3× with 200 μl of NET buffer. 40 μl of sample buffer [62.5 mM Tris-HCl/pH 6.8, 10% (V/V) glycerol, 2% (W/V) sodium dodecylsulfate, 5% (V/V) β-mercaptoethanol, 0.02% (W/V) Bromophenol Blue] was added to the pellet. The resultant suspension was boiled at 100° C. for 3 minutes and centrifuged at 12,000 r.p.m. for 1 minute to recover the supernatant which was loaded on 12% (W/V) SDS-PAGE.

Electrophoresis was carried out according to the method (Laemmli, 1970 Nature 227: 680). After electrophoresis, the gel was immersed in 10% (V/V) acetic acid for 30 minutes to fix the protein, washed in water for 30 minutes and immersed in 1M sodium salicylate for 30 minutes. The gel was dried and exposed to a X-ray film (Fuji Film Co.) for fluorography.

The film was analyzed: The presence of a band on the film indicated the presence of an elevated level of alkaline protease mRNA in that fraction.

(4) Preparation of Rabbit Anti-alkaline Protease Serum

Rabbit antiserum against purified alkaline protease was prepared as follows.

0.7 ml of alkaline protease (40 mg/ml) purified from *Aspergillus oryzae* was mixed with an equal volume of Freund's complete adjuvant. The mixture was injected to a pad of a Japanese white rabbit (2 kg). The rabbit was boosted two weeks after the first injection with the same amount of the antigen-adjuvant mixture intracutaneously at the back. One week later, the rabbit was boosted as described above. One week after the final injection, the rabbit was sacrificed and bled.

The blood was left standing at 4° C. for 18 hours and then centrifuged at 3,000 r.p.m. for 15 minutes to give a supernatant containing anti-alkaline protease serum.

(5) Synthesis of Alkaline Protease cDNA

Alkaline protease cDNA was prepared using an Amersham's kit.

cDNA was prepared from 1.6 μg of mRNA according to the method as described in Mol. Cell. Biol. 2: 161, 1982 and Gene 25: 263, 1983, as recommended by the manufacturer's instructions. 160 ng of double-stranded cDNA was obtained. The EcoRI site of the cDNA (160 ng) was methylated using a cDNA Cloning Kit (Amersham) according to the manufacturer's instructions. Then, both terminals of the cDNA were ligated with an EcoRI linker.

(6) Construction of an Alkaline Protease cDNA Library 100 ng of plasmid pUC119 DNA (Takara Shuzo) was suspended in 8 μl of water. To the suspension, 1 μl of Med reaction buffer [100 mM Tris-HCl (pH 7.5), 100 mM MgCl$_2$, 10 mM dithiothreitol, 500 mM NaCl] and then 1 μl of EcoRI (10 unit) (Takara Shuzo) were added, and the mixture was incubated at 37° C. for 2 hours.

1 μl of 1M Tris-HCl (pH 8.0) and 1 μl of alkaline phosphatase (0.3 unit, Takara Shuzo) were added to the digest. The mixture was incubated at 65° C. for 1 hour to dephosphorylate both terminals of the digest. Then 12 μl of water-equilibrated phenol was added to the mixture to remove proteins. To the aqueous phase, 1 μl of 3M sodium acetate (pH 5.8) and 26 μl of ice cold ethanol were added. The mixture was allowed to stand at −70° C. for 15 minutes, and then centrifuged with a microfuge (MRX-150, Tomy Seiko Co.) at 12,000 r.p.m. for 5 minutes to give DNA.

100 ng of plasmid pUC119 DNA thus obtained and 160 ng of cDNA prepared as described in Section (5) above were suspended in 8 μl of water. To the suspension, 1 μl of 10× ligation buffer (200 mM MgCl$_2$, 66 mM Tris-HCl/pH 7.6, 10 mM ATP, 150 mM dithiothreitol) and 1 μl of T4 DNA ligase (Takara Shuzo) (1 unit) were added. The mixture was incubated at 16° C. for 16 hours to effect ligation.

The resulting construct was used to transform E. coli DH1 (ATCC 33849) according to the method described by Hanahan in DNA Cloning, 1: 109–135 (1985). A cDNA library was thus constructed using the plasmid pUC119 vector.

(7) Screening of Alkaline Protease cDNA Fragment

The screening of an alkaline protease cDNA fragment was carried out according to the hybridization selection method (Molecular Cloning, 1982, Cold Spring Harbor, Cold Spring Harbor Laboratory p329) as follows.

70 transformants selected randomly from the cDNA library (Section (6)) were screened for the presence of an alkaline protease cDNA as described below. 500 μg of recombinant plasmid DNA was prepared from E. coli strains according to the method (Molecular Cloning, 1982, Cold Spring Harbor, Cold Spring Harbor Laboratory p86). 100 μg of the recombinant DNA was suspended in 200 μl of water and incubated at 100° C. for 10 minutes, then cooled on ice. 1M sodium hydroxide was added to the suspension. The mixture was incubated at room temperature for 20 minutes to denature the recombinant plasmid DNA.

200 μl of a neutralizing solution [1M NaCl, 0.3M sodium citrate, 0.5M Tris-HCl/pH 8.0, 1M HCl] was added to the denatured DNA mixture immediately after the incubation. The mixture was mixed well and cooled on ice. The mixture was then filtered using a round nitrocellulose filter (5 mm in diameter, Cat. No, HAWP 02500, Millipore) and the filter was air-dried. The filter was washed with 6×SSC (0.9M NaCl, 0.09M sodium citrate), air-dried and baked in a vacuum oven at 80° C. for 2 hours. Thus, the recombinant plasmid DNA was fixed on the filter.

The filter was immersed in 10 μl of hybridization buffer {100 μg/ml of mRNA as prepared in Section (2), 65% (V/V) deionized formamide, 20 mM 1,4-piperazinediethanesulfonic acid/pH 6.4, 0.2% sodium dodecylsulfate, 0.4M NaCl, 100 μg/ml of yeast t-RNA} and incubated at 50° C. for 3 hours. The mRNA in the hybridization buffer was hybridized to plasmid DNA on the filter. The filter was then washed 9× with 1 ml of wash I [10 mM Tris-HCl/pH 7.6, 0.15M NaCl, 1 mM EDTA, 0.5% sodium dodecylsulfate] and 2× with 1 ml of wash II [10 mM Tris-HCl/pH 7.6, 0.15M NaCl, 1 mM EDTA]. The washing procedure removed unhybridized mRNA.

The filter was then placed in 100 μl of water in a tube. 10 μg of yeast tRNA was added to the tube which was then placed in hot water at 100° C. for 1 minute. The tube was then placed in a dry ice/ethanol bath, removed from the bath and left standing at room temperature. mRNA hybridized to the plasmid DNA immobilized on the filter was thus dissociated from the filter. 10 μl of 3M sodium acetate (pH 5.2) and 300 μl of ice cold ethanol were added to the solution containing mRNA. The mixture was incubated at −70° C. for 1 hour, then centrifuged with a microfuge (MRX-150, Tomy Seiko Co.) at 12,000 r.p.m. for 5 minutes. After centrifugation, mRNA was recovered.

In vitro translation was carried out using mRNA as described in Section (3) and a polypeptide synthesized was analyzed using anti-alkaline protease serum as prepared in Section (4).

One positive colony was found in the 70 transformants. The plasmid (designated pOAP3) was regarded as containing the alkaline protease cDNA fragment derived from Aspergillus oryzae (ATCC 20386).

1 μg of pOAP3 DNA was digested with EcoRI, and pBR322 DNA (Takara Shuzo Co. LTD) was digested with AluI. The restriction fragments were electrophoresed on an agarose gel and the band patterns were compared. It has been found that a 750 bp fragment containing an alkaline protease cDNA was incorporated in pOAP3.

(8) Screening of Larger DNA Fragment Containing Alkaline Protease cDNA From the Library The 750 bp band was excised from the agarose gel described in Section (7) and put into a dialysis tube. 500 μl of TE buffer [10 mM Tris-HCl (pH 8.0), 1 mM EDTA] was added to the tube which was then sealed and subjected to electrophoresis to allow DNA out from the gel into the TE buffer. After electroelution, an equal volume of water-equilibrated phenol was added to the TE buffer containing DNA. The aqueous phase was recovered, and 100 ng of alkaline protease cDNA was harvested using the ethanol precipitation method known in the art. 100 ng of the DNA was labelled with α-$^{32}$P dCTP (Amersham) by nick translation according to the method described in J. Mol. Biol., 113: 237–251, 1977 and Molecular Cloning, p. 109–112, 1982. The $^{32}$P-labelled DNA was used as a probe for screening the alkaline protease cDNA from the library as described in Section (6) according to the colony hybridization method [Protein, Nucleic Acid and Enzyme, 1981 26: 575–579]. One positive colony was obtained, and designated pOAP5. The plasmid DNA of pOAP5 was isolated according to the method described in Section (7).

An E. coli DH1 transformant harboring the plasmid pOAP5 was designated E. coli DH1 pOAP5. E. coli DH1 (pOAP5) was deposited with Fermentation Research Institute, Agency of Industrial Science and Technology and was assigned the accession number FERM P-9870.

Plasmid pOAP5 DNA was digested with EcoRI as described in Section (6), followed by agarose gel electrophoresis. The inserted DNA fragment was followed to be 1,100 bp in length. 100 ng of the 1,100 bp DNA containing the alkaline protease cDNA was obtained by isolation and purification as described in Section (8). DNA thus obtained was digested with one or two enzymes of the member EcoRI, AflII, KpnI, SalI, and XmnI. The sizes of the bands were compared as described in section (7), and a restriction map of pOAP5 was constructed and is shown in FIG. 1.

(9) Sequencing of Alkaline Protease cDNA

Plasmids pUC18 and pUC19 (Takara Shuzo Co. LTD) were digested with the same restriction enzyme(s) as used for the digestion of the 1,100 bp fragment of pOAP5. The restriction fragments of the 1,100 bp fragment were ligated with a plasmid vector having the same restriction site. The constructs containing the restriction fragment was subjected to alkaline denaturation as described by Sakaki in Vector DNA, p. 70, Kodansha, 1986, and then sequenced using a M13 Sequence Kit (Takara Shuzo) according to dideoxy chain termination method known in the art.

The sequence of the alkaline protease cDNA fragment from *Aspergillus oryzae* (ATCC 20386) was determined. The nucleotide sequence of the mature alkaline protease gene is shown in the Sequence Listing defined by SEQ ID NO: 2, and the deduced amino acid sequence is shown in the Sequence Listing defined by SEQ ID NO: 3.

Purified alkaline protease had 16 amino acids as defined in the Sequence Listing by SEQ ID NO: 4 at the N-terminus, which corresponded to the predicted amino acid sequence (residues 1-16 of the sequence in the Sequence Listing defined by SEQ ID NO: 3).

It can be concluded from the above findings that the nucleotide sequence as defined by the Sequence Listing by SEQ ID NO: 2 encodes the amino acid sequence from N-terminal to C-terminal of alkaline protease.

Figure 2:
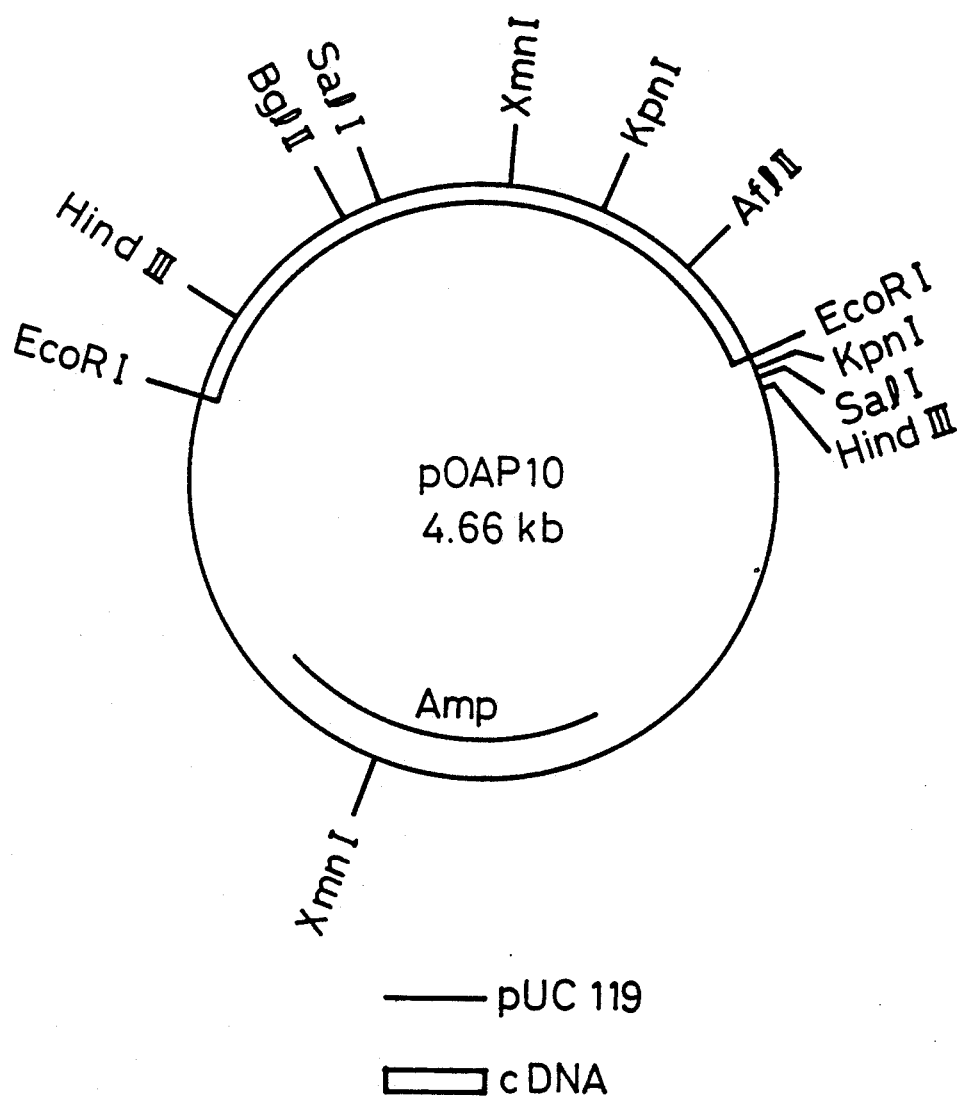
FIG. 2 shows the restriction map of recombinant plasmid pOAP10.

(10) Screening of DNA Fragment Containing Alkaline Protease Gene and Its Prepro Sequence The nucleotide sequence analysis revealed that pOAP5 contained the DNA fragment encoding the amino acid sequence between N-terminal and C-terminal of mature alkaline protease but lacked a prepro sequence which was believed to be located upstream of the alkaline protease gene. An alkaline protease cDNA fragment of pOAP5 was cleaved and labelled with $^{32}P$ using a nick translation method as described in Section (8). The labelled probe was used to screen the cDNA library as described in (6) according to colony hybridization method. Colonies containing the larger fragment comprising an alkaline protease cDNA were found and one of them was designated pOAP10, and *E. coli* DH1 transformant harboring plasmid pOAP10 was designated *E. coli* DH1 (pOAP10). DNA was prepared, digested with EcoRI and electrophoresed on an agarose gel as described in Section (7). It was shown that a 1,500 bp DNA fragment was inserted in pOAP10. pOAP10 DNA was digested one or two enzymes from the group consisting of AFlII, EcoRI, KpnI, SalI, XmnI, BglII and HindIII. The band patterns were analyzed as described in (7). The restriction map of pOAP10 DNA was constructed and is shown in FIG. 2.

(11) Sequencing of DNA Fragment Containing Full-Length Alkaline Protease Gene Plasmids pUC18 and pUC19 were digested with the same restriction enzyme(s) as used for the digestion of the 1,500 bp fragment of pOAP10. The restriction fragments of the 1,500 bp fragment were ligated with a plasmid vector having the same restriction site, according to the method as described in (9). Sequencing of the constructs was carried out using the dideoxy chain termination method as described in (9).

The alkaline protease and prepro sequence of *Aspergillus oryzae* (ATCC 20386) are shown in the Sequence Listing defined by SEQ ID NO: 5, wherein nucleotide numbers 53(A)-415(T) are the sequence of a prepro region and nucleotide numbers 416(G)-1261(T) are the sequence of the alkaline protease gene.

Deduced amino acid sequence is shown in the Sequence Listing defined by SEQ ID NO: 6. The number of amino acid is 403. The amino acid sequence experimentally determined suggests that 16 amino acids as defined in the Sequence Listing by SEQ ID NO: 4 at the N-terminal of alkaline protease correspond to the deduced amino acid sequence starting from the amino acid number 122 (residues 122-137 of the sequence in the Sequence Listing defined by SEQ ID NO: 6). An amino acid sequence extending from N-terminal to the amino acid number 121 constitutes a prepro region necessary for secretion of alkaline protease, and the region of amino acid numbers 122-403 constitutes mature alkaline protease.

Thus, the nucleotide sequence as defined in the Sequence Listing by SEQ ID NO: 5 encodes an entire amino acid sequence comprising the prepro and mature alkaline protease sequences.

(12) Preparation of Single-Stranded DNA from pOAP10

Single-stranded DNA was prepared from *E. coli* DH1 (pOAP10) according to the method (Methods in Enzymology, 153: 3-11)

(13) Synthesis of Oligonucleotides

To introduce mutation into pOAP10, oligonucleotides A and B were synthesized using DNA synthesizer (System 1E plus DNA Synthesizer, Beckman). The nucleotide sequences of A and B oligomer are as defined in the Sequence Listing by SEQ ID NO: 7 and NO: 8, respectively.

(14) Introduction of Mutation into Alkaline Protease cDNA

A site-directed mutation was introduced into pOAP10 using oligomer A or B using Oligonucleotide-Directed in vitro Mutagenesis System Version 2 (Amersham) according to the manufacturer's instructions. The plasmids thus obtained were designated pOAP30 and pOAP31, respectively.

(15) Sequencing of Mutants

Plasmid DNA of the mutants was subjected to alkaline denaturation as described by Sakaki in Vector DNA, 1986, Kodansha p70, and then sequenced using a MB Sequence kit (Takara Shuzo Co. LTD) according to the dideoxy chain termination method. GTG (nucleotide numbers 118-120) of wild type alkaline protease gene was replaced by ATT in mutant pOAP30 and by CTG in mutant pOAP31.

(16) Construction of Expression Vector

The 1.5 kb EcoRI fragment (alkaline protease gene + prepro sequence) of pOAP10 (Japanese Patent Application No. 280373/1988) was inserted into an EcoRI site of AAR6 (Washington Research Foundation) which was a boundary between an ADH1 promoter and terminator. The construct was designated pOAP103. The replication origin (ARS1) of pOAP103 was replaced by the one of 2μ DNA since ARS1 was expected to be unstable in a yeast host; AAH5 (Washington Research Foundation) containing a replication origin of 2μ DNA and pOAP103 were digested with BamHI. The restriction fragments were ligated and the construct was designated pOAP107. pOAP107 contained Leu2, a selectable marker, which made the size of the construct too large (14.2 kb). To reduce the size of the construct, Leu2 was replaced by TRP1 of MA56 (Washington Research Foundation); pOAP107 and MA56 were digested with PstI. The restriction fragments were ligated and the construct was designated pOAP108 (ADH1 promoter, alkaline protease cDNA and its prepro sequence, ADH1 terminator, replication origin of 2μ DNA and a TRP marker.

Figure 3:
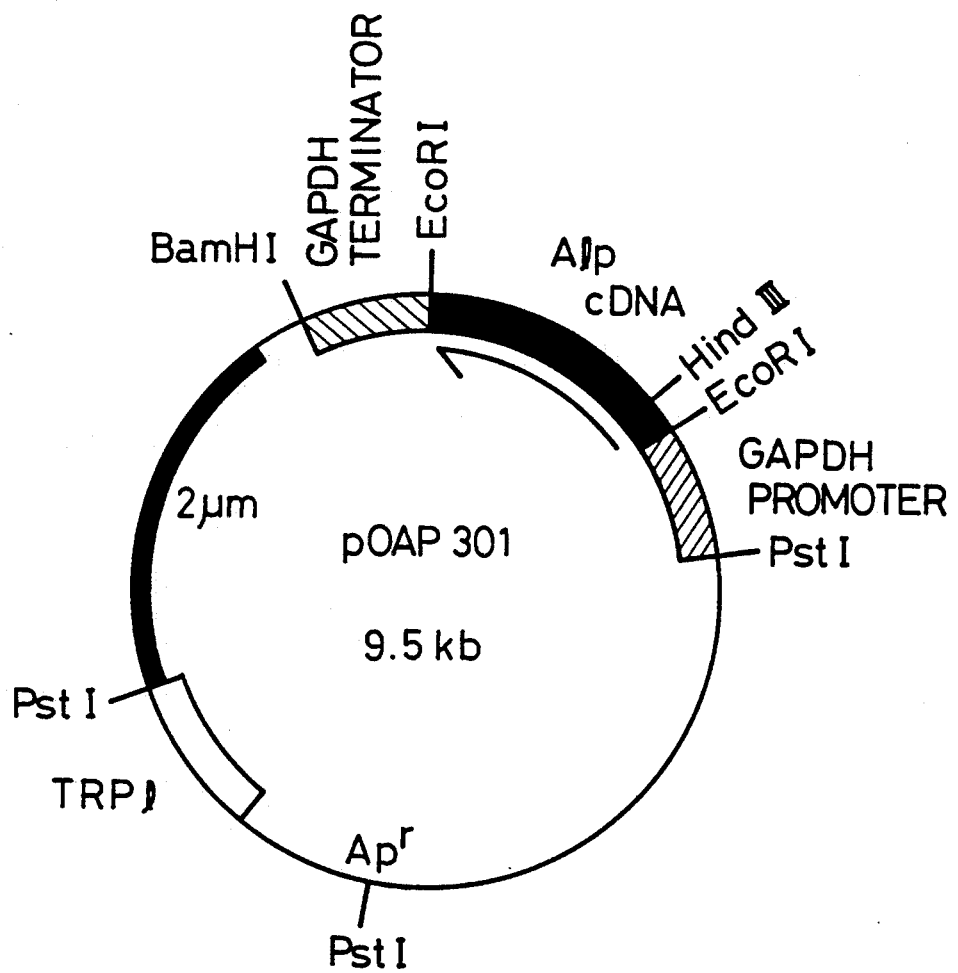
FIG. 3 shows the restriction map of recombinant plasmid pOAP301.
Figure 4:
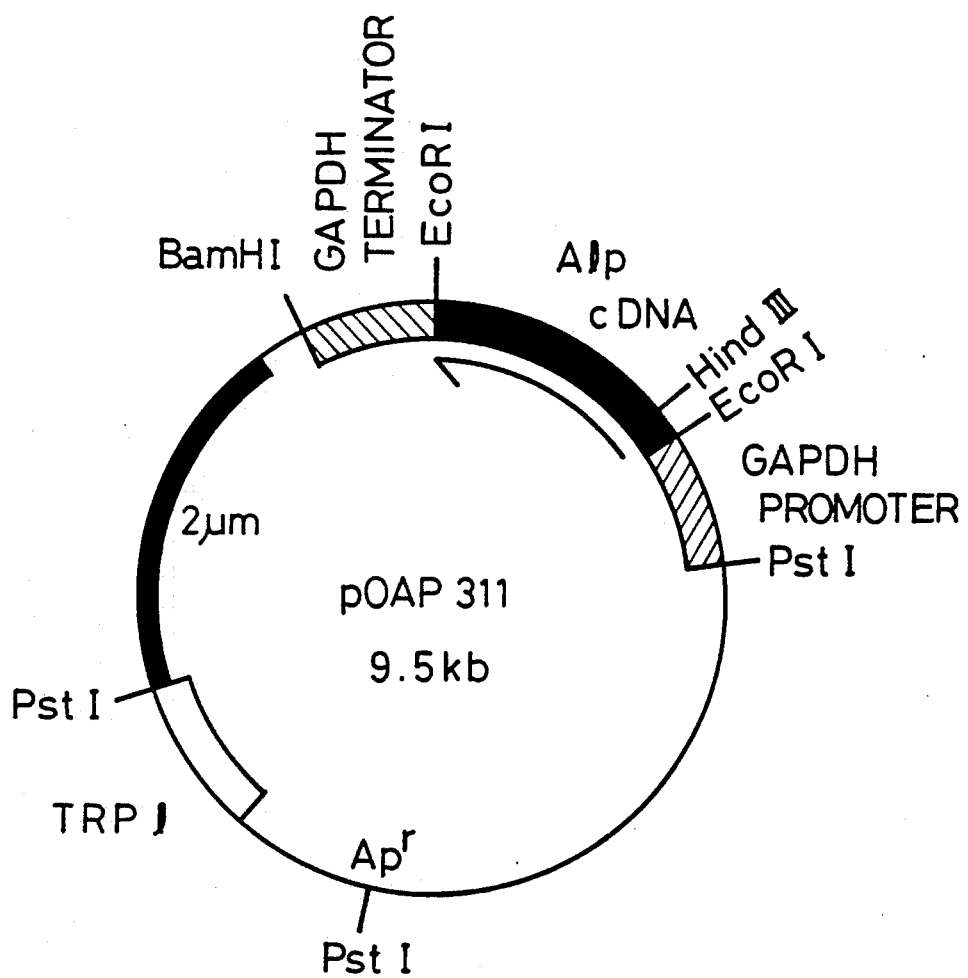
FIG. 4 shows the restriction map of recombinant plasmid pOAP311.

The GAPDH promoter of pT143 (generous gift from Prof. Toe of Hiroshima University) which was derived from *Zygosaccharomyces rouxii* was inserted into pUC19; The EcoRI-PstI fragment containing the GAPDH promoter sequence except for 4 nucleotides just upstream of the transcription initiation site was inserted into the EcoRI-PstI site of pUV19. The construct was designated pUG43. In order to insert the GAPDH terminator of *Zygosaccharomyces rouxii* into pUG43, the SspI site of pUG43 was converted into a BamHI site. The resultant construct was designated pUBG43. The GAPDH terminator and its 700 bp downstream sequence of pGAP4-Zr (generous gift from Prof. Toe of Hiroshima University) were inserted in pUBG43; pGAP4-Zr and pUBG43 were digested with EcoRI and BamHI. The fragments were ligated and the construct was designated pUGT43. In pUGT43, the GAPDH promoter was located at one side of a EcoRI site and the GAPDH terminator at the other side of the EcoRI site. The 1.5 kb EcoRI fragment containing alkaline protease cDNA of pOAP10 was inserted into the EcoRI site of pUGT43. The construct was designated pGAT43 (GAPDH promoter, 1.5 kb EcoRI fragment and GAPDH terminator + 700 bp sequence).

pOAP108 and pGAT43 were digested with BamHI and SphI. The fragment containing the replication origin of 2μ DNA and a selectable marker (TRP-1) of pOAP108 and the fragment containing a GAPDH promoter, an alkaline protease gene + prepro sequence, and a GAPDH terminator + 700 bp sequence of pGAT43 were ligated. The construct was designated pOAP106B.

pOAP30 and pOAP31 which contained mutation in an alkaline protease gene, and pOAP106B were digested with BglII and AflII (Takara Shuzo Co. LTD). After digestion, a 8.9 kb DNA fragment of pOAP106B was obtained by electroelution. The 860 bp DNA fragment of pOAP30 or pOAP31 encoding mature alkaline protease and the 8.9 kb fragment of pOAP106B were ligated. The construct containing the 860 bp fragment of pOAP30 or pOAP31 was designated pOAP301 or pOAP311, respectively. The restriction maps of pOAP301 and pOAP311 are shown in FIG. 3 and FIG. 4, respectively.

(17) Transformation of Yeast with Recombinant Plasmid pOAP301 or pOAP311

*Saccharomyces cerevisiae* NA87-11A (generous gift from Prof. Oshima of Osaka University) was transformed with pOAP301 or pOAP311 according to the method described by Beggs (Nature, 1978, 275: 104–109). The respective transformants were designated *Saccharomyces cerevisiae* NA87-11A (pOAP301) and (pOAP311).

*Saccharomyces cerevisiae* NA87-11A (pOAP301) and (pOAP311) were deposited with Fermentation Research Institute, Agency of Industrial Science and Technology, Ministry of International Trade and Industry, 1-3, Higashi 1-chome, Tsukuba-shi, Ibaraki-ken, Japan (Postal Code: 305), and were assigned the accession number FERM P-11345 (FERM BP-3298) and FERM P-11346(FERM BP-3299), respectively.

(18) Production of Alkaline Protease Using Transformants,

*Saccharomyces cerevisiae* NA87-11A pOAP301 (FERM P-11345) and pOAP311 (FERM P-11346)

*Saccharomyces cerevisiae* NA87-11A pOAP301 (FERM P-11345) and pOAP311 (FERM P-11346) were inoculated into 3 ml of YPD medium (20 g/l of glucose, 20 g/l of polypeptone, 10 g/l of yeast extract) in respective tubes. The tubes were incubated with shaking at 30° C. for 16 hours. 1 ml of the resultant culture was centrifuged at 3,000 r.p.m. for 5 minutes using MRX-150 Centrifuge (Tomy Seiko Co. Ltd.).

The supernatant thus obtained was tested for alkaline protease activity according to the method described by Y. Fukushima et al., Agric. Biol. Chem. 49: 1643–1648 (1985) and modified by Annson and Hagiwara, and alkaline protease activity of *S. cerevisiae* pOAP301 and pOAP311 was both 1.7 P.U./ml (protease units per milliliter). As a control, similar procedure as described above was repeated using *Saccharomyces cerevisiae* NA87-11A containing plasmid pOAP106B. The alkaline protease activity of the control was found to be less than 0.1 P.U./ml.

As evident from the above description, the culture obtained according to the present process has markedly increased alkaline protease activity as compared with the control, indicating that alkaline protease was produced by culturing the above mentioned transformant yeast and secreted into the culture medium.

(19) Purification of Alkaline Protease

Alkaline protease was purified according to the method (T. Nakadai, 1973, Agric. Biol. Chem. 37: 2685-2694). Valine at the amino acid number 40 of wild type alkaline protease was replaced by leucine or isoleucine in the products from the mutants. The physical and chemical properties of alkaline protease produced by the mutants were the same as those of the wild type. However, the alkaline protease produced by the mutants exhibit 1.6- or 1.7-fold increased activity as compared with a wild type. The yield of alkaline protease produced by the mutants were 16,000 P.U. and 20,000 P.U., respectively.

Various references have been cited in the specification, the disclosures of which are incorporated herein, in their entirety, by reference.

What is claimed is:

1. A mutant alkaline protease which is a mutant of a wild-type alkaline protease having the sequence shown in SEQ ID No: 3, wherein amino acid number 40 of said wild-type alkaline protease is replaced by leucine or isoleucine.

2. A gene encoding the amino acid sequence of a mutant alkaline protease which is a mutant of a wild-type alkaline protease having the sequence shown in SEQ ID No: 3, wherein amino acid number 40 of said wild-type alkaline protease is replaced by leucine or isoleucine.

3. A recombinant DNA molecule which comprises a gene inserted into a vector, said gene encoding the amino acid sequence of a mutant alkaline protease which is a mutant of a wild-type alkaline protease having the sequence shown in SEQ ID No: 3, wherein amino acid number 40 of said wild-type alkaline protease is replaced by leucine or isoleucine.

4. A method of producing alkaline protease which comprises:

culturing a microorganism belonging to the genus Saccharomyces which harbors recombinant DNA encoding the amino acid sequence of a mutant alkaline protease, which is a mutant of a wild-type alkaline protease having the sequence shown in SEQ ID No: 3 in which amino acid number 40 of said wild-type alkaline protease is replaced by leucine or isoleucine, under conditions in which the mutant alkaline protease is expressed, and recovering the mutant alkaline protease which is expressed.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Aspergillus oryzae
        ( B ) STRAIN: ATCC 20386

( i x ) FEATURE:
        ( A ) NAME/KEY: CDS
        ( B ) LOCATION: 1..846

( x i ) SEQUENCE DESCRIPTION: SEQ ID NO:1:

```
Met Gln Ser Ile Lys Arg Thr Leu Leu Leu Gly Ala Ile Leu Pro
 1               5                  10                  15

Ala Val Leu Gly Ala Pro Val Gln Glu Thr Arg Arg Ala Ala Glu Lys
                20                  25                  30

Leu Pro Gly Lys Tyr Ile Val Thr Phe Lys Pro Gly Ile Asp Glu Ala
             35                  40                  45

Lys Ile Gln Glu His Thr Thr Trp Ala Thr Asn Ile His Gln Arg Ser
     50                  55                  60

Leu Glu Arg Arg Gly Ala Thr Gly Gly Asp Leu Pro Val Gly Ile Glu
 65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp
            115                 120
```

( 2 ) INFORMATION FOR SEQ ID NO:2:

( i ) SEQUENCE CHARACTERISTICS:
        ( A ) LENGTH: 846 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Aspergillus oryzae
        ( B ) STRAIN: ATCC 20386

( i x ) FEATURE:
        ( A ) NAME/KEY: CDS
        ( B ) LOCATION: 1..846

( x i ) SEQUENCE DESCRIPTION: SEQ ID NO:2:

```
GGC CTG ACT ACC CAG AAG AGT GCC CCC TGG GGT CTG GGC AGC ATT TCC        48
Gly Leu Thr Thr Gln Lys Ser Ala Pro Trp Gly Leu Gly Ser Ile Ser
 1               5                  10                  15

CAC AAG GGC CAG CAG AGC ACC GAC TAC ATC TAC GAC ACT AGT GCC GGC        96
His Lys Gly Gln Gln Ser Thr Asp Tyr Ile Tyr Asp Thr Ser Ala Gly
                20                  25                  30

GAG GGC ACC TAT GCC TAC GTG GTG GAT AGC GGT GTC AAT GTC GAC CAT       144
Glu Gly Thr Tyr Ala Tyr Val Val Asp Ser Gly Val Asn Val Asp His
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  |  | 45 |  |  |  |  |
| GAG | GAG | TTC | GAG | GGC | CGC | GCC | AGC | AAG | GCC | TAC | AAC | GCT | GCC | GGT | GGT |
| Glu | Glu | Phe | Glu | Gly | Arg | Ala | Ser | Lys | Ala | Tyr | Asn | Ala | Ala | Gly | Gly |
|  | 50 |  |  |  | 55 |  |  |  |  | 60 |  |  |  |  |  |

192

| CAG | CAT | GTG | GAC | AGC | ATT | GGC | CAT | GGC | ACC | CAC | GTT | TCC | GGC | ACC | ATT |
|---|---|---|---|---|---|---|---|---|---|---|---|---|---|---|---|
| Gln | His | Val | Asp | Ser | Ile | Gly | His | Gly | Thr | His | Val | Ser | Gly | Thr | Ile |
| 65 |  |  |  |  | 70 |  |  |  |  | 75 |  |  |  |  | 80 |

240

| GCT | GGC | AAG | ACT | TAT | GGT | ATC | GCC | AAG | AAG | GCC | AGC | ATC | CTT | TCG | GTC |
|---|---|---|---|---|---|---|---|---|---|---|---|---|---|---|---|
| Ala | Gly | Lys | Thr | Tyr | Gly | Ile | Ala | Lys | Lys | Ala | Ser | Ile | Leu | Ser | Val |
|  |  |  |  | 85 |  |  |  |  | 90 |  |  |  |  | 95 |  |

288

| AAA | GTT | TTC | CAG | GGT | GAA | TCG | AGC | AGC | ACT | TCC | GTC | ATT | CTT | GAC | GGC |
|---|---|---|---|---|---|---|---|---|---|---|---|---|---|---|---|
| Lys | Val | Phe | Gln | Gly | Glu | Ser | Ser | Ser | Thr | Ser | Val | Ile | Leu | Asp | Gly |
|  |  |  | 100 |  |  |  |  | 105 |  |  |  |  | 110 |  |  |

336

| TTC | AAC | TGG | GCT | GCC | AAC | GAC | ATT | GTT | AGC | AAG | AAG | CGT | ACC | AGC | AAG |
|---|---|---|---|---|---|---|---|---|---|---|---|---|---|---|---|
| Phe | Asn | Trp | Ala | Ala | Asn | Asp | Ile | Val | Ser | Lys | Lys | Arg | Thr | Ser | Lys |
|  |  | 115 |  |  |  |  | 120 |  |  |  |  | 125 |  |  |  |

384

| GCT | GCA | ATC | AAC | ATG | AGC | TTG | GGC | GGT | GGC | TAC | TCT | AAG | GCT | TTC | AAC |
|---|---|---|---|---|---|---|---|---|---|---|---|---|---|---|---|
| Ala | Ala | Ile | Asn | Met | Ser | Leu | Gly | Gly | Gly | Tyr | Ser | Lys | Ala | Phe | Asn |
| 130 |  |  |  |  | 135 |  |  |  |  | 140 |  |  |  |  |  |

432

| GAT | GCG | GTC | GAG | AAC | GCA | TTC | GAG | CAG | GGT | GTT | CTC | TCG | GTT | GTC | GCT |
|---|---|---|---|---|---|---|---|---|---|---|---|---|---|---|---|
| Asp | Ala | Val | Glu | Asn | Ala | Phe | Glu | Gln | Gly | Val | Leu | Ser | Val | Val | Ala |
| 145 |  |  |  |  | 150 |  |  |  |  | 155 |  |  |  |  | 160 |

480

| GCC | GGT | AAC | GAG | AAC | TCT | GAT | GCC | GGC | CAA | ACC | AGC | CCT | GCC | TCT | GCC |
|---|---|---|---|---|---|---|---|---|---|---|---|---|---|---|---|
| Ala | Gly | Asn | Glu | Asn | Ser | Asp | Ala | Gly | Gln | Thr | Ser | Pro | Ala | Ser | Ala |
|  |  |  |  | 165 |  |  |  |  | 170 |  |  |  |  | 175 |  |

528

| CCT | GAT | GCC | ATC | ACT | GTT | GCC | GCT | ATC | CAG | AAG | AGC | AAC | AAC | CGC | GCC |
|---|---|---|---|---|---|---|---|---|---|---|---|---|---|---|---|
| Pro | Asp | Ala | Ile | Thr | Val | Ala | Ala | Ile | Gln | Lys | Ser | Asn | Asn | Arg | Ala |
|  |  |  | 180 |  |  |  |  | 185 |  |  |  |  | 190 |  |  |

576

| AGT | TTC | TCC | AAC | TTT | GGC | AAG | GTC | GTT | GAC | GTC | TTC | GCT | CCC | GGT | CAA |
|---|---|---|---|---|---|---|---|---|---|---|---|---|---|---|---|
| Ser | Phe | Ser | Asn | Phe | Gly | Lys | Val | Val | Asp | Val | Phe | Ala | Pro | Gly | Gln |
|  |  | 195 |  |  |  |  | 200 |  |  |  |  | 205 |  |  |  |

624

| GAT | ATC | CTT | TCT | GCC | TGG | ATT | GGC | TCT | TCC | TCT | GCC | ACC | AAC | ACC | ATC |
|---|---|---|---|---|---|---|---|---|---|---|---|---|---|---|---|
| Asp | Ile | Leu | Ser | Ala | Trp | Ile | Gly | Ser | Ser | Ser | Ala | Thr | Asn | Thr | Ile |
| 210 |  |  |  |  | 215 |  |  |  |  | 220 |  |  |  |  |  |

672

| TCT | GGT | ACC | TCC | ATG | GCT | ACT | CCC | CAC | ATT | GTC | GGC | CTG | TCC | CTC | TAC |
|---|---|---|---|---|---|---|---|---|---|---|---|---|---|---|---|
| Ser | Gly | Thr | Ser | Met | Ala | Thr | Pro | His | Ile | Val | Gly | Leu | Ser | Leu | Tyr |
| 225 |  |  |  |  | 230 |  |  |  |  | 235 |  |  |  |  | 240 |

720

| CTC | GCT | GCC | CTT | GAG | AAC | CTC | GAT | GGC | CCC | GCT | GCC | GTG | ACC | AAG | CGC |
|---|---|---|---|---|---|---|---|---|---|---|---|---|---|---|---|
| Leu | Ala | Ala | Leu | Glu | Asn | Leu | Asp | Gly | Pro | Ala | Ala | Val | Thr | Lys | Arg |
|  |  |  |  | 245 |  |  |  |  | 250 |  |  |  |  | 255 |  |

768

| ATC | AAG | GAG | TTG | GCC | ACC | AAG | GAC | GTC | GTC | AAG | GAT | GTT | AAG | GGC | AGC |
|---|---|---|---|---|---|---|---|---|---|---|---|---|---|---|---|
| Ile | Lys | Glu | Leu | Ala | Thr | Lys | Asp | Val | Val | Lys | Asp | Val | Lys | Gly | Ser |
|  |  |  |  | 260 |  |  |  |  | 265 |  |  |  |  | 270 |  |

816

| CCT | AAC | CTG | CTT | GCC | TAC | AAC | GGT | AAC | GCT |
|---|---|---|---|---|---|---|---|---|---|
| Pro | Asn | Leu | Leu | Ala | Tyr | Asn | Gly | Asn | Ala |
|  |  | 275 |  |  |  |  | 280 |  |  |

846

( 2 ) INFORMATION FOR SEQ ID NO:3:

( i ) SEQUENCE CHARACTERISTICS:
    ( A ) LENGTH: 282 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

| Gly | Leu | Thr | Thr | Gln | Lys | Ser | Ala | Pro | Trp | Gly | Leu | Gly | Ser | Ile | Ser |
|---|---|---|---|---|---|---|---|---|---|---|---|---|---|---|---|
| 1 |  |  |  | 5 |  |  |  |  | 10 |  |  |  |  | 15 |  |

| His | Lys | Gly | Gln | Gln | Ser | Thr | Asp | Tyr | Ile | Tyr | Asp | Thr | Ser | Ala | Gly |
|---|---|---|---|---|---|---|---|---|---|---|---|---|---|---|---|
|  |  |  | 20 |  |  |  |  | 25 |  |  |  |  | 30 |  |  |

| Glu | Gly | Thr | Tyr | Ala | Tyr | Val | Val | Asp | Ser | Gly | Val | Asn | Val | Asp | His |
|---|---|---|---|---|---|---|---|---|---|---|---|---|---|---|---|
|  |  |  | 35 |  |  |  |  | 40 |  |  |  |  | 45 |  |  |

```
Glu  Glu  Phe  Glu  Gly  Arg  Ala  Ser  Lys  Ala  Tyr  Asn  Ala  Ala  Gly  Gly
     50                  55                  60

Gln  His  Val  Asp  Ser  Ile  Gly  His  Gly  Thr  His  Val  Ser  Gly  Thr  Ile
65                       70                  75                            80

Ala  Gly  Lys  Thr  Tyr  Gly  Ile  Ala  Lys  Ala  Ser  Ile  Leu  Ser  Val
                    85                       90                       95

Lys  Val  Phe  Gln  Gly  Glu  Ser  Ser  Thr  Ser  Val  Ile  Leu  Asp  Gly
                    100                 105                      110

Phe  Asn  Trp  Ala  Ala  Asn  Asp  Ile  Val  Ser  Lys  Lys  Arg  Thr  Ser  Lys
          115                      120                      125

Ala  Ala  Ile  Asn  Met  Ser  Leu  Gly  Gly  Gly  Tyr  Ser  Lys  Ala  Phe  Asn
     130                      135                      140

Asp  Ala  Val  Glu  Asn  Ala  Phe  Glu  Gln  Gly  Val  Leu  Ser  Val  Val  Ala
145                      150                      155                      160

Ala  Gly  Asn  Glu  Asn  Ser  Asp  Ala  Gly  Gln  Thr  Ser  Pro  Ala  Ser  Ala
               165                      170                      175

Pro  Asp  Ala  Ile  Thr  Val  Ala  Ala  Ile  Gln  Lys  Ser  Asn  Asn  Arg  Ala
               180                      185                      190

Ser  Phe  Ser  Asn  Phe  Gly  Lys  Val  Val  Asp  Val  Phe  Ala  Pro  Gly  Gln
          195                 200                      205

Asp  Ile  Leu  Ser  Ala  Trp  Ile  Gly  Ser  Ser  Ser  Ala  Thr  Asn  Thr  Ile
210                           215                      220

Ser  Gly  Thr  Ser  Met  Ala  Thr  Pro  His  Ile  Val  Gly  Leu  Ser  Leu  Tyr
225                      230                      235                      240

Leu  Ala  Ala  Leu  Glu  Asn  Leu  Asp  Gly  Pro  Ala  Ala  Val  Thr  Lys  Arg
               245                      250                      255

Ile  Lys  Glu  Leu  Ala  Thr  Lys  Asp  Val  Lys  Asp  Val  Lys  Gly  Ser
               260                      265                      270

Pro  Asn  Leu  Leu  Ala  Tyr  Asn  Gly  Asn  Ala
          275                      280
```

( 2 ) INFORMATION FOR SEQ ID NO:4:

( i ) SEQUENCE CHARACTERISTICS:
           ( A ) LENGTH: 16 amino acids
           ( B ) TYPE: amino acid
           ( D ) TOPOLOGY: linear ( i i ) MOLECULE TYPE: peptide ( v ) FRAGMENT TYPE: N-terminal ( v i ) ORIGINAL SOURCE:
           ( A ) ORGANISM: Aspergillus oryzae
           ( B ) STRAIN: ATCC 20386

( x i ) SEQUENCE DESCRIPTION: SEQ ID NO:4:

```
Gly  Leu  Thr  Thr  Gln  Lys  Ser  Ala  Pro  Trp  Gly  Leu  Gly  Ser  Ile  Ser
1                   5                        10                       15
```

( 2 ) INFORMATION FOR SEQ ID NO:5:

( i ) SEQUENCE CHARACTERISTICS:
           ( A ) LENGTH: 1486 base pairs
           ( B ) TYPE: nucleic acid
           ( C ) STRANDEDNESS: single
           ( D ) TOPOLOGY: linear ( i i ) MOLECULE TYPE: cDNA ( v i ) ORIGINAL SOURCE:
           ( A ) ORGANISM: Aspergillus oryzae
           ( B ) STRAIN: ATCC 20386

( i x ) FEATURE:
    ( A ) NAME/KEY: miscfeature
    ( B ) LOCATION: 53..415

( i x ) FEATURE:
    ( A ) NAME/KEY: miscfeature
    ( B ) LOCATION: 416..1261

( x i ) SEQUENCE DESCRIPTION: SEQ ID NO:5:

```
TTTCTATCCT CCGACTTGAG TTGTTCTTGC GCATCTTTAC AATCTTCTCA TCATGCAGTC      60
CATCAAGCGT ACCTTGCTCC TCCTCGGAGC TATCCTTCCC GCGGTCCTCG GTGCCCCTGT     120
GCAGGAAACC CGCCGGGCCG CTGAGAAGCT TCCTGGAAAG TACATTGTCA CATTCAAGCC     180
CGGCATTGAC GAGGCAAAGA TTCAGGAGCA TACCACCTGG GCTACCAACA TTCACCAGCG     240
CAGTCTGGAG CGTCGTGGCG CCACTGGCGG TGATCTTCCT GTCGGTATTG AGCGCAACTA     300
CAAGATCAAC AAGTTCGCCG CCTATGCAGG CTCTTTCGAC GATGCTACCA TTGAGGAGAT     360
TCGCAAGAAC GAAGATGTTG CCTACGTCGA GGAGGACCAG ATCTACTACC TCGATGGCCT     420
GACTACCCAG AAGAGTGCCC CCTGGGGTCT GGGCAGCATT TCCCACAAGG CCAGCAGAG     480
CACCGACTAC ATCTACGACA CTAGTGCCGG CGAGGGCACC TATGCCTACG TGGTGGATAG     540
CGGTGTCAAT GTCGACCATG AGGAGTTCGA GGGCCGCGCC AGCAAGGCCT ACAACGCTGC     600
CGGTGGTCAG CATGTGGACA GCATTGGCCA TGGCACCCAC GTTTCCGGCA CCATTGCTGG     660
CAAGACTTAT GGTATCGCCA AGAAGGCCAG CATCCTTTCG GTCAAAGTTT TCCAGGGTGA     720
ATCGAGCAGC ACTTCCGTCA TTCTTGACGG CTTCAACTGG GCTGCCAACG ACATTGTTAG     780
CAAGAAGCGT ACCAGCAAGG CTGCAATCAA CATGAGCTTG GGCGGTGGCT ACTCTAAGGC     840
TTTCAACGAT GCGGTCGAGA ACGCATTCGA GCAGGGTGTT CTCTCGGTTG TCGCTGCCGG     900
TAACGAGAAC TCTGATGCCG GCCAAACCAG CCCTGCCTCT GCCCTGATG CCATCACTGT     960
TGCCGCTATC CAGAAGAGCA ACAACCGCGC CAGTTTCTCC AACTTTGGCA AGGTCGTTGA    1020
CGTCTTCGCT CCCGGTCAAG ATATCCTTTC TGCCTGGATT GGCTCTTCCT CTGCCACCAA    1080
CACCATCTCT GGTACCTCCA TGGCTACTCC CCACATTGTC GGCCTGTCCC TCTACCTCGC    1140
TGCCCTTGAG AACCTCGATG CCCCGCTGC CGTGACCAAG CGCATCAAGG AGTTGGCCAC    1200
CAAGGACGTC GTCAAGGATG TTAAGGGCAG CCCTAACCTG CTTGCCTACA CGGTAACGC    1260
TTAAGTACCA GGAGTACGTC GCAGGATTCT ACCATTGTTA CTGGAATACA ATGATGATTA    1320
GAAAACGAAG AGCGTTATGA TTCGGACGGA TATATGCATG CACCCATAC AGCGTGATAC    1380
ATAGGCTGTT TGCTCAAGAA TTAGGATTTT ATCTGAATCC ATGTACAGAG TATACTTATG    1440
TTAGTAGTCA ATAAAATCTT GGCTTTCTAA AAAAAAAAAA AAAAAA                  1486
```

( 2 ) INFORMATION FOR SEQ ID NO:6:

( i ) SEQUENCE CHARACTERISTICS:
        ( A ) LENGTH: 403 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Aspergillus oryzae
        ( B ) STRAIN: ATCC 20386

( i x ) FEATURE:
        ( A ) NAME/KEY: miscfeature
        ( B ) LOCATION: 1..121

( i x ) FEATURE:
        ( A ) NAME/KEY: miscfeature
        ( B ) LOCATION: 122..403

(xi) SEQUENCE DESCRIPTION: SEQ ID NO:6:

```
Met Gln Ser Ile Lys Arg Thr Leu Leu Leu Leu Gly Ala Ile Leu Pro
 1               5                  10                  15

Ala Val Leu Gly Ala Pro Val Gln Glu Thr Arg Arg Ala Ala Glu Lys
                20                  25                  30

Leu Pro Gly Lys Tyr Ile Val Thr Phe Lys Pro Gly Ile Asp Glu Ala
                35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
                100                 105                 110

Glu Glu Asp Gln Ile Tyr Tyr Leu Asp Gly Leu Thr Thr Gln Lys Ser
            115                 120                 125

Ala Pro Trp Gly Leu Gly Ser Ile Ser His Lys Gly Gln Gln Ser Thr
        130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
                180                 185                 190

His Gly Thr His Val Ser Gly Thr Ile Ala Gly Lys Thr Tyr Gly Ile
            195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
                260                 265                 270

Glu Gln Gly Val Leu Ser Val Val Ala Ala Gly Asn Glu Asn Ser Asp
            275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
                340                 345                 350

Pro His Ile Val Gly Leu Ser Leu Tyr Leu Ala Ala Leu Glu Asn Leu
            355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

(2) INFORMATION FOR SEQ ID NO:7:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (vi) ORIGINAL SOURCE:
  (A) ORGANISM: Aspergillus oryzae
  (B) STRAIN: ATCC 20386

(xi) SEQUENCE DESCRIPTION: SEQ ID NO:7:

GCCTACGTGA TTGATAGCGG T         21

(2) INFORMATION FOR SEQ ID NO:8:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (vi) ORIGINAL SOURCE:
  (A) ORGANISM: Aspergillus oryzae
  (B) STRAIN: ATCC 20386

(xi) SEQUENCE DESCRIPTION: SEQ ID NO:8:

GCCTACGTGC TGGATAGCGG T         21